(12) United States Patent
Berglund et al.

(10) Patent No.: US 9,523,014 B2
(45) Date of Patent: Dec. 20, 2016

(54) PROCESS FOR GRINDING CELLULOSE ETHER

(75) Inventors: Lars Erik Berglund, Domsjö (SE); Birgit Tora Gunvor Karlsson, Stenungsund (SE)

(73) Assignee: AKZO NOBEL N.V., Arnhem (NL)

( * ) Notice: Subject to any disclaimer, the term of this patent is extended or adjusted under 35 U.S.C. 154(b) by 1050 days.

(21) Appl. No.: 11/913,891

(22) PCT Filed: May 9, 2006

(86) PCT No.: PCT/EP2006/062159
§ 371 (c)(1),
(2), (4) Date: Nov. 8, 2007

(87) PCT Pub. No.: WO2006/120194
PCT Pub. Date: Nov. 16, 2006

(65) Prior Publication Data
US 2008/0207893 A1 Aug. 28, 2008

(30) Foreign Application Priority Data
May 12, 2005 (EP) .................................... 05103978

(51) Int. Cl.
| | | |
|---|---|---|
| *C08B 11/20* | (2006.01) | |
| *C08L 3/12* | (2006.01) | |
| *C04B 40/00* | (2006.01) | |
| *C09D 101/28* | (2006.01) | |
| *A61K 47/38* | (2006.01) | |
| *C04B 24/38* | (2006.01) | |
| *C04B 28/14* | (2006.01) | |
| *C08B 11/193* | (2006.01) | |
| *C08J 3/12* | (2006.01) | |
| *C08L 1/28* | (2006.01) | |
| *C04B 103/44* | (2006.01) | |
| *C04B 111/00* | (2006.01) | |

(52) U.S. Cl.
CPC ............. *C09D 101/28* (2013.01); *A61K 47/38* (2013.01); *C04B 24/383* (2013.01); *C04B 28/14* (2013.01); *C04B 40/0039* (2013.01); *C08B 11/193* (2013.01); *C08B 11/20* (2013.01); *C08J 3/124* (2013.01); *C08L 1/28* (2013.01); *C04B 2103/44* (2013.01); *C04B 2111/00482* (2013.01); *C08J 2301/28* (2013.01)

(58) Field of Classification Search
CPC ............ C08L 1/26; C08L 1/28; C04B 24/383; C08B 40/0039

USPC ...................................... 536/86, 124; 514/57
See application file for complete search history.

(56) References Cited

U.S. PATENT DOCUMENTS

| | | | |
|---|---|---|---|
| 2,720,464 A | 10/1955 | Anderson et al. | |
| 4,076,935 A | 2/1978 | Eichenseer et al. | |
| 4,329,451 A | 5/1982 | Zweigle | |
| 4,540,499 A * | 9/1985 | Sakatani et al. | 510/515 |
| 4,707,189 A * | 11/1987 | Nickol | 106/173.01 |
| 4,747,550 A | 5/1988 | Jackering | |
| 5,921,479 A * | 7/1999 | Doenges et al. | 241/18 |
| 6,165,965 A * | 12/2000 | Schalitz et al. | 510/384 |
| 6,197,100 B1 * | 3/2001 | Melbouci | 106/174.1 |
| 6,509,461 B2 | 1/2003 | Schlesiger et al. | |
| 7,635,662 B2 * | 12/2009 | Kabashima et al. | 503/222 |

FOREIGN PATENT DOCUMENTS

| | | |
|---|---|---|
| DE | 1 068 685 | 11/1959 |
| DE | 38 11 910 C2 | 10/1997 |
| DE | 10201344 A1 * | 9/2003 |
| EP | 0 347 948 A2 | 12/1989 |
| EP | 0 775 526 B1 | 5/1997 |
| EP | 0 991 668 B1 | 4/2000 |
| EP | 1 117 694 B1 | 7/2001 |
| GB | 1224390 A * | 3/1971 |
| GB | 1 514 788 | 6/1978 |
| GB | 2 262 527 A | 6/1993 |
| JP | 54050025 A * | 4/1979 |
| JP | 2001323299 A * | 11/2001 |

OTHER PUBLICATIONS

International Search Report for International Application No. PCT/EP2006/062159, Aug. 9, 2006.
European Search Report for International Application No. PCT/EP05/103978, Sep. 15, 2005.
HCAPLUS Abstract of DE1068685.
Abstract No. 89-310409/43 for DE3811910C2.
Brochure: "Product overview Surfactants Europe" Jun. 2002, Akzo Nobel N.V.; pp. 42.

* cited by examiner

*Primary Examiner* — Sudhakar Katakam
*Assistant Examiner* — Everett White
(74) *Attorney, Agent, or Firm* — Sandra B. Weiss

(57) ABSTRACT

The invention relates to a process for grinding cellulose ether comprising the steps of: a) grinding a cellulose ether comprising 20 to 90 wt % of water, based on the total weight of cellulose ether and water, and a cationic surfactant in a mill; and b) optionally drying the mixture while grinding, prior to or following the step of grinding.

13 Claims, No Drawings

PROCESS FOR GRINDING CELLULOSE ETHER

This case was filed under the Patent Cooperation Treaty on May 9, 2006 and claims priority of European Application No. 05103978.2 filed on May 12, 2005 and U.S. Provisional Application No. 60/693,657 filed on Jun. 24, 2005.

The invention relates to a process for grinding cellulose ether.

Such a process is known from U.S. Pat. No. 6,509,461, wherein a feed composition of swollen and/or dissolved cellulose derivative and water is contacted with a carrier and heat exchange gas, such as air or a steam/air mixture, in a sieve-free high rotational speed gas jet impact mill.

U.S. Pat. No. 4,076,935 describes a process for grinding cellulose compounds using a vibration mill in the presence of air and sufficient water to yield a product having a water content of from 2 to 10 percent by weight (wt %).

U.S. Pat. No. 2,720,464 discloses cellulose ether compositions comprising cellulose ether and a surface-active agent. The surface-active agent can be sodium lauryl sulfate. The cellulose ether compositions are in the form of dry powders, which are prepared by first drying the composition and subsequently grinding it.

DE 1 068 685 discloses a process for grinding cellulose ether in the presence of a surface-active compound using a hammer mill. The surface-active agent is sprayed over the cellulose ether inside the hammer mill while the cellulose ether is being ground.

The processes of the prior art have the problem that the moist cellulose ether agglomerates and/or adheres to the walls of the mill causing loss of product. Furthermore, the products obtained with these processes exhibit a considerable risk of dust explosions upon handling and when stored.

The object of the present invention is to provide an improved process for grinding cellulose ether and to provide a cellulose ether product with a reduced risk of dust explosions.

This object is achieved by a process for grinding cellulose ether comprising the steps of:
 a) grinding a cellulose ether comprising 20 to 90 wt % of water, based on the total weight of cellulose ether and water, and a cationic surfactant in a mill; and
 b) optionally drying the mixture while grinding, prior to or following the step of grinding.

The process of the invention results in finely sized products that are antistatic and hence do not cluster or agglomerate. A further advantage is that the cellulose ether does not stick to the walls of the mill, rendering a higher product yield. The use of cationic surfactants leads to cellulose ether compositions which are less biodegradable than compositions comprising anionic surfactants, which is particularly advantageous in applications where good stability against (bio)degradation is important, for example in wall paper adhesive applications. The improved biodegradability may effect a longer storage life of stock solutions of the cellulose ether. Additionally, due to their positive charge the cationic surfactants are able to adsorb to the cellulose ether more efficiently than anionic surfactants, resulting in a finely sized cellulose ether product which is more antistatic, exhibits less clustering, and reduces the risk of dust explosion upon handling and storage.

The cellulose ether used in the process of the invention comprises 20-90 wt % water, based on the total weight of the cellulose ether and water. Preferably, the cellulose ether comprises 25-85 wt % water, more preferably 30-80 wt % water, and most preferably 40-80 wt % water.

The cellulose ether of the present invention can be any cellulose ether known in the art. The cellulose ether can be non-ionic and anionic. Examples of non-ionic cellulose ethers are methyl cellulose, hydroxyethyl cellulose, methyl hydroxyethyl cellulose, ethyl hydroxyethyl cellulose, methyl ethyl hydroxyethyl cellulose, hydroxypropyl hydroxyethyl cellulose, methyl hydroxypropyl hydroxyethyl cellulose, hydroxypropyl cellulose, methyl hydroxypropyl cellulose, and ethyl hydroxypropyl cellulose. Examples of anionic cellulose ethers are carboxymethyl cellulose, hydroxyethyl carboxymethyl cellulose, hydroxypropyl carboxymethyl cellulose, sulfoethyl cellulose, hydroxyethyl sulfoethyl cellulose, and hydroxypropyl sulfoethyl cellulose. Further examples of these cellulose ethers are hydrophobically modified cellulose ethers, which are also known in the art, for example from EP 0 991 668 and EP 1 117 694. Also mixtures of any of the above cellulose ethers can be used in the process of the invention.

The cationic surfactant can be any cationic surfactant known in the art. Preferably, the cationic surfactant is a quaternary ammonium compound. The cationic surfactant may be a quaternary ammonium compound according to the formulae I-III:

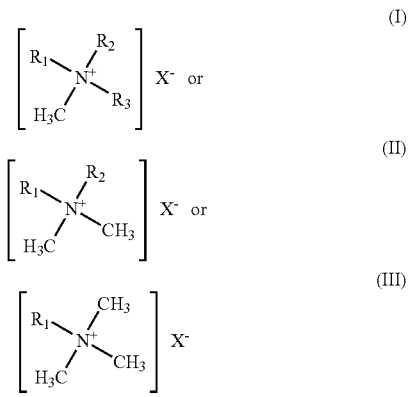

wherein $R_1$ to $R_3$ are the same or different and are hydrocarbons having from 8 to 22 carbon atoms, or at least one of $R_1$-$R_3$ is a polyethoxylate group having from 2 to 20 EO units and the remaining groups of $R_1$ to $R_3$ are hydrocarbons having from 8 to 22 carbon atoms, and $X^{-1}$ is an anion selected from chlorine, bromide or methylsulfate. Preferably, $R_1$ to $R_3$ are hydro-carbons having from 10 to 20 carbon atoms.

Examples of cationic surfactants are tetradecyl trimethyl ammonium chloride, hexadecyl trimethyl ammonium chloride, coco trimethyl ammonium chloride, tallow trimethyl ammonium chloride, hydrogenated tallow trimethyl ammonium chloride, oleyl trimethyl ammonium chloride, hydrogenated tallow trimethyl ammonium methosulfate, didecyl di methyl ammonium chloride, dicoco dimethyl ammonium chloride, di(hydrogenated tallow) dimethyl ammonium chloride, ditallow dimethyl ammonium chloride, cocobenzyl dimethyl ammonium chloride, alkylpolyglycolether ammonium methyl chloride, and alkylpolyglycolether ammonium methyl sulfate. Commercial examples of cationic surfactants can be found in the brochure "Product overview Surfactants Europe" of June 2002 from Akzo Nobel N V. A preferred cationic surfactant is didecyl dimethyl ammonium chloride. This surfactant has enhanced biocidal properties compared to other cationic surfactants, enabling, if necessary, a longer storage life of the cellulose ether without it being deteriorated by bacteria.

The amount of cationic surfactant in the cellulose ether is at least 0.001 wt %, preferably at least 0.005 wt %, and most preferably at least 0.01 wt %, based on the total weight of the dry cellulose ether, and at most 1 wt %, preferably at most 0.5 wt %, and most preferably at most 0.1 wt %.

The mill used in the process of the present invention can be any mill suitable for grinding cellulose ethers. Examples of such mills are hammer mills, ball mills, vibration mills, and impact mills. In such mills a liquid, a gas flow or a combination of both can be added to and/or flown over the cellulose ether present in the mill. If a liquid or gas/liquid mixture is used, the cellulose ether can be ground under cryogenic conditions. Preferred mills are those in which a gas stream can be flown over the cellulose ether while the cellulose ether is ground. An example of such a mill is an impact mill described in EP 0 347 948, DE 38 11 910 or EP 0 775 526. The gas stream can be an inert gas (such as nitrogen and carbon dioxide), air, a mixture of inert gas and steam, or a mixture of steam and air. The gas stream may be heated, be at ambient temperature or may be cooled. Preferably, the gas stream is heated to a temperature between 100° C. and 250° C. In particular, use of a heated gas stream in the impact mill enables simultaneous grinding and effective drying of the cellulose ether, which is more cost effective and simplifies the process.

The cationic surfactant is preferably added to the cellulose ether just before the cellulose ether is introduced into the mill. In this way loss of surfactant, for example during the preparation of the cellulose ether or transport to the mill, is prevented.

The present invention further pertains to cellulose ether comprising a cationic surfactant obtainable by any of the above-mentioned processes. The amount of water in the cellulose ether of the invention is less than 10 wt %, preferably less than 6 wt %, more preferably less than 4 wt %, and most preferably less than 2 wt %, based on the weight of dry cellulose ether.

The mean particle size of the cellulose ether particles obtained with the process of the invention can be any mean particle size available in the art. The mean particle size may typically be between 0.05 and 1 mm.

The cellulose ether of the invention can be suitably used in a wide variety of applications, such as in cement, gypsum, coating compositions, as a thickening agent or as a binder in colouring agents, and in pharmaceuticals.

The invention is illustrated in the following examples.

EXAMPLES

"Plastic bag"-Test

Three portions of 100 parts by weight of ethyl hydroxyethyl cellulose (EHEC) containing 50 wt % water, calculated on the dry weight of the EHEC, were put in three plastic bags. The EHEC/water lumps have diameters of between 10 and 20 mm. In one bag (bag A) 0.01 part by weight of didecyl dimethyl ammonium chloride was added. In a second bag (bag B) 0.01 part by weight of $C_{14}$-$C_{16}$ olefin sulfonate was added. No surfactant was added in the third bag (bag C). The ingredients inside bags A to C were agitated with mechanical force on the outside of each bag.

The EHEC/water lumps in bag 1 containing cationic surfactant were well dispersed after agitation and had broken up into pieces to form particles having a diameter of 2-5 mm. No adsorption was observed on the walls of the plastic bag.

The EHEC/water lumps containing anionic surfactant in bag 2 were dispersed after agitation and had broken up into pieces to form particles having a diameter of 5-8 mm. Some solid material had adsorbed onto the inner wall of bag 2. The inner wall was further observed to be sticky.

The EHEC/water lumps without surfactant in bag 3 had agglomerated to form one big lump. The inner wall of the plastic bag was sticky.

These experiments show the EHEC/water lumps can be comminuted more easily to smaller particles by using cationic surfactant than by using an anionic surfactant or no surfactant at all.

Dry Grinding 100 parts by weight of ethyl hydroxyethyl cellulose (EHEC) containing 50 wt % water, calculated on the dry weight of the EHEC, were mixed with 0.01 part by weight of didecyl dimethyl ammonium chloride (cationic surfactant). The EHEC was well dispersed in the mixture; no lumps were observed. Subsequently, the mixture was introduced into an impact mill, where it was dried and ground to form a powder having particle size of less than 200 μm. There was no EHEC on the walls of the mill.

For comparison, the same experiment was repeated, except that no surfactant was added. Prior to introduction into the mill, the moist EHEC showed poor dispersion and big lumps were observed. Inspection of the mill after drying and grinding revealed a substantial amount of the cellulose ether sticking to the walls of the mill, rendering a lower product yield than observed when adding the cationic surfactant.

The invention claimed is:

1. A process for grinding a moist cellulose ether mixture comprising the steps of:
    a) grinding a moist cellulose ether mixture comprising 20 to 90 wt % of water, based on the total weight of cellulose ether and water, and a cationic surfactant in a mill; and
    b) optionally drying the mixture while grinding, prior to or following the step of grinding
        wherein the cellulose ether is a non-ionic cellulose ether selected from the group consisting of methyl cellulose, hydroxyethyl cellulose, methyl hydroxyethyl cellulose, ethyl hydroxyethyl cellulose, methyl ethyl hydroxyethyl cellulose, hydroxypropyl hydroxyethyl cellulose, methyl hydroxypropyl hydroxyethyl cellulose, hydroxypropyl cellulose, methyl hydroxypropyl cellulose, and ethyl hydroxypropyl cellulose; and
        wherein the cationic surfactant is a quaternary ammonium salt, and
        wherein the mean particle size of the cellulose ether after grinding is between 0.05 and 1 mm.

2. A process according to claim 1 wherein the cationic surfactant is a quaternary ammonium salt comprising at least one hydrocarbon group comprising 8 to 22 carbon atoms.

3. A process according to claim 1 wherein the cationic surfactant is present in an amount of 0.001 to 2 wt %, based on the total weight of the mixture.

4. A process according to claim 1 wherein the cationic surfactant is present in an amount of 0.01 to 0.5 wt %, based on the total weight of the mixture.

5. A process according to claim 1, wherein the cationic surfactant is present in an amount of 0.001 to 0.1 wt %, based on the total weight of the dry cellulose ether.

6. A process according to claim 5, wherein the cellulose ether mixture comprises 40 to 85 wt % of water, based on the total weight of cellulose ether and water.

7. A process according to claim 6, wherein the cationic surfactant is a quaternary ammonium salt having two methyl groups and two hydrocarbon groups comprising 8 to 22 carbon atoms all bonded to a N atom.

8. A process according to claim 7, wherein the cationic surfactant is didecyl dimethyl ammonium chloride.

9. A process according to claim 1, wherein the process comprises simultaneously grinding and drying the cellulose ether.

10. A process according to claim 1 wherein the cellulose ether mixture consists essentially of a mixture of cellulose ether, 20 to 90 wt % of water, based on the total weight of cellulose ether and water, and a cationic surfactant.

11. A process according to claim 1 wherein the cellulose ether mixture consists of a mixture of cellulose ether, 20 to 90 wt % of water, based on the total weight of cellulose ether and water, and a cationic surfactant.

12. A process for grinding a composition comprising cellulose ether/water lumps, the lumps comprising 20 to 90 wt % of water, based on the total weight of cellulose ether and water, the process comprising the steps of:
a) combining the composition comprising cellulose ether/water lumps with an amount of a cationic surfactant;
b) grinding the combined composition of step (a) in a mill; and
c) optionally drying the combined composition while grinding, prior to or following the step of grinding
wherein the cellulose ether is a non-ionic cellulose ether selected from the group consisting of methyl cellulose, hydroxyethyl cellulose, methyl hydroxyethyl cellulose, ethyl hydroxyethyl cellulose, methyl ethyl hydroxyethyl cellulose, hydroxypropyl hydroxyethyl cellulose, methyl hydroxypropyl hydroxyethyl cellulose, hydroxypropyl cellulose, methyl hydroxypropyl cellulose, and ethyl hydroxypropyl cellulose; and
wherein the cationic surfactant is a quaternary ammonium salt, and
wherein the mean particle size of the cellulose ether after grinding is between 0.05 and 1 mm.

13. The process of claim 12, wherein the cellulose ether lumps comprise 40-85 wt % water, based on the total weight of the cellulose ether and water.

* * * * *